US010685742B2

(12) United States Patent
Walker

(10) Patent No.: US 10,685,742 B2
(45) Date of Patent: *Jun. 16, 2020

(54) SYSTEM AND METHOD FOR PROVIDING IDENTIFICATION AND MEDICAL INFORMATION FROM A SUBJECT

(71) Applicant: SOLOMON SYSTEMS, INC., Springdale, MD (US)

(72) Inventor: Timothy T. Walker, Springdale, MD (US)

(73) Assignee: SOLOMON SYSTEMS, INC., Springdale, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/174,571

(22) Filed: Jun. 6, 2016

(65) Prior Publication Data

US 2016/0283668 A1 Sep. 29, 2016

Related U.S. Application Data

(63) Continuation-in-part of application No. 14/856,083, filed on Sep. 16, 2015, now Pat. No. 9,390,231, which (Continued)

(51) Int. Cl.
*G06Q 50/22* (2018.01)
*G06Q 10/06* (2012.01)
(Continued)

(52) U.S. Cl.
CPC ............ *G16H 10/60* (2018.01); *A61B 90/90* (2016.02); *A61B 90/96* (2016.02); *A61B 90/98* (2016.02);
(Continued)

(58) Field of Classification Search
CPC .......... G06K 5/00; G06K 19/00; G06K 19/06; G06K 7/08; G06K 7/01; G06F 17/00
(Continued)

(56) References Cited

U.S. PATENT DOCUMENTS 5,877,742 A 3/1999 Klink
6,681,003 B2 1/2004 Linder et al.
(Continued)

FOREIGN PATENT DOCUMENTS

| JP | 7-307803 | 11/1995 |
| JP | 2003067488 | 3/2003 |
| KR | 10-2009-0128962 | 12/2009 |

OTHER PUBLICATIONS

International Search Report of Application No. PCT/US2016/036046, dated Sep. 6, 2016.
(Continued)

*Primary Examiner* — Edwyn Labaze
(74) *Attorney, Agent, or Firm* — Ping Wang; Morris, Manning & Martin LLP

(57) ABSTRACT

A device and system for providing identification and medical information are disclosed. The device includes a readable code that contains medical biographical information of the subject, a programmable reporter element that is programmed to electronically store at least one particular event relating to the subject, and a signal producing element functionally related to the programmable reporter element. In one aspect, a method for providing identification and medical information from a subject includes providing a subject with a device comprising a Radio Frequency Identification (RFID) tag and scanning the RFID tag with the RFID reader. The RFID tag includes a chip configured to be scanned and read by an RFID reader, whereby the chip is wirelessly linked to a server containing medical and biographical information specific to the subject.

17 Claims, 5 Drawing Sheets

Related U.S. Application Data is a continuation of application No. 14/458,877, filed on Aug. 13, 2014, now Pat. No. 9,165,335, which is a continuation of application No. 13/917,374, filed on Jun. 13, 2013, now Pat. No. 8,833,649, which is a continuation of application No. 13/313,821, filed on Dec. 7, 2011, now Pat. No. 8,485,439, which is a continuation-in-part of application No. 13/270,672, filed on Oct. 11, 2011, now Pat. No. 8,181,862.

(60) Provisional application No. 62/174,206, filed on Jun. 11, 2015.

(51) Int. Cl.
| | | |
|---|---|---|
| *A61B 90/90* | (2016.01) | |
| *G06K 19/077* | (2006.01) | |
| *G16H 10/60* | (2018.01) | |
| *A61B 90/96* | (2016.01) | |
| *G06Q 50/24* | (2012.01) | |
| *A61B 90/98* | (2016.01) | |
| *G16H 10/65* | (2018.01) | |
| *G06F 19/00* | (2018.01) | |
| *G06K 19/06* | (2006.01) | |

(52) U.S. Cl.
CPC ............ *G06F 19/00* (2013.01); *G06Q 10/06* (2013.01); *G06Q 50/22* (2013.01); *G06Q 50/24* (2013.01); *G16H 10/65* (2018.01); *G06K 19/06046* (2013.01); *G06K 19/07758* (2013.01)

(58) Field of Classification Search
USPC ..... 235/380, 487, 375, 382.5, 382, 451, 492
See application file for complete search history.

(56) References Cited

U.S. PATENT DOCUMENTS

| | | | |
|---|---|---|---|
| 6,751,805 B1 | 6/2004 | Austion | |
| 7,204,808 B1 | 4/2007 | Friedman et al. | |
| 7,434,724 B2 | 10/2008 | Lane | |
| 7,515,053 B2 | 4/2009 | Klein | |
| 7,761,261 B2 | 7/2010 | Shmueli et al. | |
| 8,405,518 B2 | 3/2013 | Corwin et al. | |
| 2001/0045469 A1 | 11/2001 | Hooglander | |
| 2003/0016122 A1 | 1/2003 | Petrick | |
| 2003/0052788 A1 | 3/2003 | Kwong-Tai Chung | |
| 2003/0058110 A1* | 3/2003 | Rich ................ | G08B 13/2462 340/573.1 |
| 2003/0149526 A1* | 8/2003 | Zhou ................ | G01S 5/0027 701/408 |
| 2004/0104271 A1 | 6/2004 | Martucci et al. | |
| 2004/0140898 A1 | 7/2004 | Reeves | |
| 2004/0151071 A1 | 8/2004 | Kocher | |
| 2005/0052275 A1 | 3/2005 | Houle | |
| 2006/0106646 A1* | 5/2006 | Squilla ................ | G06F 19/322 705/3 |
| 2007/0046476 A1 | 3/2007 | Hinkamp | |
| 2007/0074043 A1 | 3/2007 | Lacey | |
| 2007/0156452 A1 | 7/2007 | Batch | |
| 2007/0158411 A1 | 7/2007 | Krieg | |
| 2007/0159309 A1* | 7/2007 | Ito .................... | G06F 19/363 340/425.5 |
| 2007/0229287 A1 | 10/2007 | Morgan | |
| 2007/0233520 A1 | 10/2007 | Wehba et al. | |
| 2008/0099550 A1* | 5/2008 | Engel ................ | G06F 19/323 235/376 |
| 2008/0109260 A1* | 5/2008 | Roof ................. | G06F 19/3406 705/3 |
| 2008/0131362 A1 | 6/2008 | Rousso et al. | |
| 2008/0200774 A1 | 8/2008 | Luo | |
| 2008/0228045 A1* | 9/2008 | Gao ................... | A61B 5/0024 600/301 |
| 2008/0303638 A1 | 12/2008 | Nguyen et al. | |
| 2009/0058635 A1* | 3/2009 | LaLonde ........... | A61N 1/37282 340/539.11 |
| 2009/0138281 A1 | 5/2009 | Hacker | |
| 2009/0143045 A1* | 6/2009 | Graves .............. | A61B 5/02055 455/404.1 |
| 2009/0230179 A1 | 9/2009 | Livolsi et al. | |
| 2009/0256701 A1* | 10/2009 | Chamberlain ........ | G06Q 50/22 340/539.12 |
| 2009/0273455 A1* | 11/2009 | Sweeney ............. | A61B 5/1113 340/286.07 |
| 2009/0322513 A1 | 12/2009 | Hwang et al. | |
| 2010/0072280 A1 | 3/2010 | McGill et al. | |
| 2010/0088252 A1 | 4/2010 | Le-Henand et al. | |
| 2010/0123547 A1* | 5/2010 | Stevenson ................ | A61N 1/08 340/5.61 |
| 2010/0298899 A1 | 11/2010 | Donnell et al. | |
| 2010/0315225 A1* | 12/2010 | Teague ................ | A61B 5/0024 340/539.12 |
| 2010/0324936 A1* | 12/2010 | Vishnubhatla ........ | G06F 19/328 705/3 |
| 2011/0003610 A1 | 1/2011 | Key et al. | |
| 2011/0057037 A1 | 3/2011 | Frysz et al. | |
| 2011/0092825 A1 | 4/2011 | Gopinathan et al. | |
| 2011/0127325 A1 | 6/2011 | Hussey et al. | |
| 2011/0130636 A1* | 6/2011 | Daniel ................ | G08B 25/016 600/301 |
| 2011/0185178 A1* | 7/2011 | Gotthardt .............. | H04L 9/3231 713/172 |
| 2011/0240729 A1 | 10/2011 | Shuck | |
| 2012/0011565 A1* | 1/2012 | Garlie ................ | G06F 21/6245 726/2 |
| 2012/0078068 A1* | 3/2012 | Ulmer ................ | A61B 5/0031 600/302 |
| 2012/0179908 A1 | 7/2012 | Duma | |
| 2012/0181333 A1* | 7/2012 | Krawczewicz .... | G06K 19/0718 235/380 |
| 2012/0203076 A1* | 8/2012 | Fatta ................ | A61B 5/681 600/300 |
| 2013/0056535 A1 | 3/2013 | Rowlandson et al. | |
| 2013/0290013 A1 | 10/2013 | Forrester | |
| 2014/0039932 A1 | 2/2014 | Walton, III | |
| 2014/0070012 A1 | 3/2014 | Hunt et al. | |
| 2014/0159912 A1* | 6/2014 | Fraden ................ | A61B 5/002 340/870.02 |
| 2015/0087232 A1* | 3/2015 | Sloan ................ | G06F 19/3418 455/41.2 |
| 2015/0224243 A1* | 8/2015 | Elahi ................. | A61M 1/28 604/29 |
| 2015/0234986 A1* | 8/2015 | Dantsker ............. | G06F 19/324 705/2 |

OTHER PUBLICATIONS

Ngail, E., et al., "Design of an RFID-based Healthcare Management System using an Information System Design Theory", Inf Syst Front, 2009, 11:405-417.
International Search Report and Written Opinion of the International Searching Authority issued in International Patent Application Serial No. PCT/US2012/052089 dated Jan. 21, 2013.
File history of U.S. Appl. No. 13/313,821, filed Dec. 7, 2011.
File history of U.S. Appl. No. 13/270,672, filed Oct. 11, 2011.
File history of U.S. Appl. No. 13/917,374, filed Jun. 13, 2013.
File history of U.S. Appl. No. 14/458,877, filed Aug. 13, 2014.
File history of U.S. Appl. No. 14/856,083, filed Sep. 16, 2015.

\* cited by examiner

SYSTEM AND METHOD FOR PROVIDING IDENTIFICATION AND MEDICAL INFORMATION FROM A SUBJECT

This application is a Continuation-in-Part of U.S. patent application Ser. No. 14/856,083, filed on Sep. 16, 2015, which is a Continuation of U.S. patent application Ser. No. 14/458,877, filed on Aug. 13, 2014, now U.S. Pat. No. 9,165,335, which is a Continuation of U.S. patent application Ser. No. 13/917,374, filed on Jun. 13, 2013, now U.S. Pat. No. 8,833,649, which is a Continuation of U.S. patent application Ser. No. 13/313,821, filed Dec. 7, 2011, now U.S. Pat. No. 8,485,439, which is a Continuation-In-Part of U.S. patent application Ser. No. 13/270,672, filed Oct. 11, 2011, now U.S. Pat. No. 8,181,862. This application further claims priority to U.S. Provisional Application Ser. No. 62/174,206, filed Jun. 11, 2015. The entirety of the aforementioned applications is incorporated herein by reference.

FIELD

This application generally relates to relates to a system and method for providing identification and/or medical information from a subject in medical emergencies, for filling prescriptions and for managing a subject medical information records.

BACKGROUND

When a subject, to whom lacks the ability to effectively communicate needs urgent medical care, responders typically arrive at the scene within a short period of time without any information regarding the person in distress (i.e., subject). To properly provide medical care, the responders typically ask the subject relevant questions, such as current medications, allergies to medications, prior medical histories, i.e. surgeries, hospital visits, and other conditions. However, even if the subject is alert, he or she typically cannot provide accurate answers to such questions under the circumstances. Consequently, responders often provide urgent medical care without some medical history information. Likewise, after the subject is transported to a medical facility, doctors and other medical personnel at the hospital are not equipped with some of the medical history information regarding the subject, especially if the subject has never gone to the hospital before. Medical personnel may need to contact the subject's physician and/or other hospitals to get the needed information, which can cost time, and potentially life. Therefore, it is a great need for a system which can provide biographical information and allows medical professionals to obtain a subject's medical information.

Additionally, there exists a need for such a system, wherein the system further comprises an integrated element that can remind the subject of upcoming events related to their care and alert practitioners when the subject fails to fulfill those events.

SUMMARY

One aspect of the present application relates to a removable device that is adapted to be worn or in the possession of the subject, wherein the device comprises: a readable code that contains medical biographical information of the subject, a programmable reporter element that is programmed to electronically store at least one particular event relating to the subject, and a signal producing element functionally related to the programmable reporter element.

Another aspect of the present application relates to a system for providing identification and medical information of a subject in a removable device, comprising: a database for collecting and storing medical biographical information of the subject; a removable device that is adapted to be worn or in the possession of the subject, wherein the device comprises: a readable code that contains medical biographical information of the subject, a programmable reporter element that is programmed to electronically store at least one particular event relating to the subject, and a signal producing element functionally related to the programmable reporter element; and an appliance for scanning the readable code of the device worn by or in the possession of the subject to retrieve medical biographical information of the subject, wherein the retrieved medical biographical information allows responders to obtain the subject's medical information in order to provide care.

Another aspect of the present application relates to a non-transitory computer readable medium providing instructions for providing identification and medical information, the instructions comprising: collecting and storing medical biographical information of a subject; embedding the medical biographical information in a readable code of a removable device that is adapted to be worn by or in the possession of the subject; scanning the readable code of the device worn by or in the possession of the subject using an appliance to retrieve the medical biographical information of the subject; wherein the medical biographical information allows responders to obtain the subject's medical information in order to provide medical care and wherein the device is not linked to a medical sensor and is worn by the subject in a non-hospital setting; and programming a reporter element that provides a signal to a functionally linked signal producing element to inform the subject of at least one particular event relating to the subject, wherein said programming is by a second system that electronically stores at least one particular event relating to the subject.

In another aspect, a method for providing identification and medical information from a subject includes providing a subject with a device comprising a Radio Frequency Identification (RFID) tag and scanning the RFID tag with the RFID reader. The RFID tag includes a chip configured to be scanned and read by an RFID reader, whereby the chip is wirelessly linked to a server containing medical and biographical information specific to the subject.

In some embodiments, the device is contained in an object worn by the subject. This can allow for access ready access in cases where the subject is incapacitated and in need of medical attention.

In other embodiments, the device includes an insurance card comprising the RFID tag.

The server may include any medical or biographical information specific for the subject. Examples of medical records or personal information may include, for example, records of previous lab work, x-rays, CT-scans or MRIs, any known allergies, blood type, height, weight, date of birth, social security number, last known address, known illnesses, diseases, medical procedures or operations performed, medications previously or currently prescribed, listed Primary Care Provider (PCP), contact information from the subject, contact information from the subject's next of kin and combinations thereof.

In some embodiments, the method further includes retrieving the subject's medical and biographical information from the server; displaying the subject's medical and biographical information on the screen of the RFID reader;

and/or treating the subject based on a consideration of the subject's medical and biographical information.

In some embodiments, the method further includes selecting a suitable receiving hospital from a group of facilities listed on the device and notifying an emergency department in the selected receiving hospital of the subject's pending arrival at the receiving hospital. In some embodiments, the method may include providing the subject's medical and biographical information obtained from the server to the emergency department, along with a description of the treatment provided to the subject. Alternatively, or in addition, the method may further include notifying one or more of the subject's next of kin concerning the subject's emergency visit to the hospital.

In some embodiments, the subject is automatically registered in the receiving hospital following transmission of the medical or biographical information from the server.

In some embodiments, the method includes the steps of retrieving the subject's medical and biographical information from the server; displaying the subject's medical and biographical information on the screen of the RFID reader; and prescribing one or drugs for the subject based on a consideration of the subject's medical and biographical information.

In other embodiments, the method includes the steps of checking into a hospital or registering for a medical appointment, based on identification of the subject's RFID tag; and retrieving the subject's medical and biographical information from the server. The subject's medical and biographical information may then be displayed on the screen of the RFID reader.

In some embodiments, the subject's medical and biographical information may be downloaded into an electronic medical records (EMR) database. In other embodiments, medical information pertaining to the subject's hospital visit or medical appointment may be entered into the EMR database.

Another aspect of the present application relates to a portable device for storing medical information from a subject. The portable device comprises (a) a solid-state memory that stores medical information of the subject; (b) a readable code on a surface of the device for identification; and (c) an interface to interact with a computer, smart phone or tablet.

BRIEF DESCRIPTION OF THE DRAWINGS

The detailed description will refer to the following drawings, wherein like numerals refer to like elements.

DETAILED DESCRIPTION

Figure 1:
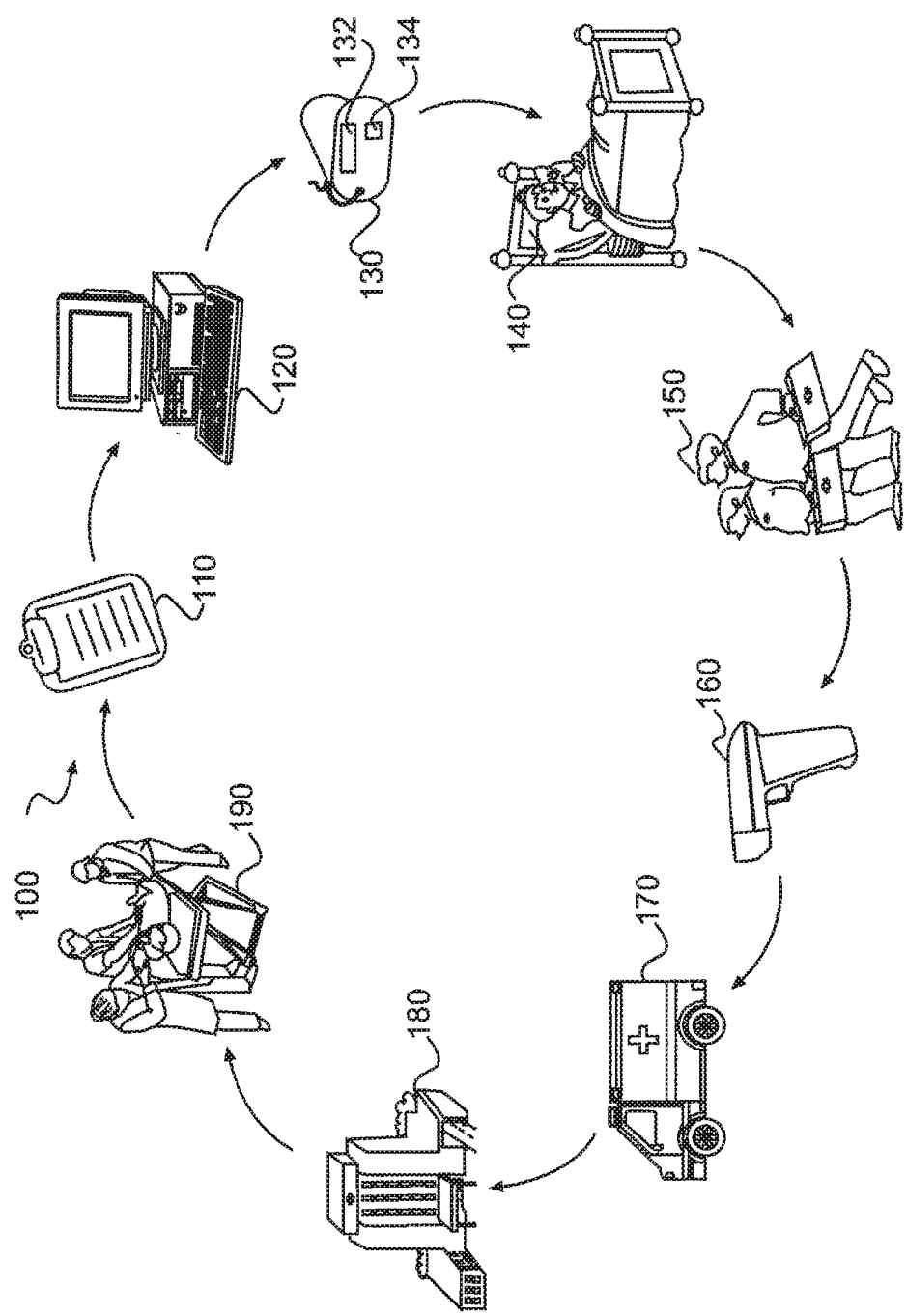
FIG. 1 illustrates an embodiment of the system for providing identification and medical information.

The following detailed description is presented to enable any person skilled in the art to make and use the invention.

For purposes of explanation, specific nomenclature is set forth to provide a thorough understanding of the present invention. However, it will be apparent to one skilled in the art that these specific details are not required to practice the invention.

Descriptions of specific applications are provided only as representative examples. The present application is not intended to be limited to the embodiments shown, but is to be accorded the widest possible scope consistent with the principles and features disclosed herein.

One aspect of the present application relates to a removable device that is adapted to be worn or in the possession of the subject, wherein the device comprises: a readable code that contains medical biographical information of the subject, a programmable reporter element that is programmed to electronically store at least one particular event relating to the subject, and a signal producing element functionally related to the programmable reporter element.

In particular embodiments, the device is not linked to a medical sensor and is worn by the subject in a non-hospital setting.

In particular embodiments, said reporter element is programmed by a second system that electronically stores at least one particular event relating to the subject. In a further embodiment, the second system additionally alerts a medical practitioner if the subject fails to fulfill the event.

In particular embodiments, the event is an appointment. In a further embodiment, said appointment is a medical appointment. In a still further embodiment, said medical appointment is selected from the group consisting of a physical examination, a physical therapy session, a mental examination and a mental therapy session. In another further embodiment, said appointment is a follow-up to a visit by the subject to a medical facility.

In particular embodiments, the reporter element is programmed to issue a signal a predetermined time prior to the at least one particular event. In a further embodiment, the signal repeats or remains until the subject fulfills the event and the reporter element is reset. In a still further embodiment, the reporter element is reset by a medical practitioner.

In particular embodiments, the device further comprises a tracking circuit that is capable of tracking the subject's location.

In particular embodiments, the medical biographical information includes one or more of the subject's name, sex, date of birth, height, weight, blood type, allergies, sicknesses or medical conditions, use of medications, emergency contacts, and complete medical records.

In particular embodiments, the device is a bracelet or a necklace worn by the subject.

Another aspect of the present application relates to a system for providing identification and medical information of a subject in a removable device, comprising: a database for collecting and storing medical biographical information of the subject; a removable device that is adapted to be worn or in the possession of the subject, wherein the device comprises: a readable code that contains medical biographical information of the subject, a programmable reporter element that is programmed to electronically store at least one particular event relating to the subject, and a signal producing element functionally related to the programmable reporter element; and an appliance for scanning the readable code of the device worn by or in the possession of the subject to retrieve medical biographical information of the subject, wherein the retrieved medical biographical information allows responders to obtain the subject's medical information in order to provide care.

In particular embodiments, the system further comprises a computer screen located in an emergency vehicle to display the retrieved medical biographical information.

In particular embodiments, the system further comprises transmitting the retrieved medical biographical information to a medical facility that is designated to receive the subject.

In particular embodiments, the medical biographical information is updated after the subject is treated at the medical facility.

Another aspect of the present application relates to a non-transitory computer readable medium providing instructions for providing identification and medical information, the instructions comprising: collecting and storing medical biographical information of a subject; embedding the medical biographical information in a readable code of a removable device that is adapted to be worn by or in the possession of the subject; scanning the readable code of the device worn by or in the possession of the subject using an appliance to retrieve the medical biographical information of the subject; wherein the medical biographical information allows responders to obtain the subject's medical information in order to provide medical care and wherein the device is not linked to a medical sensor and is worn by the subject in a non-hospital setting; and programming a reporter element that provides a signal to a functionally linked signal producing element to inform the subject of at least one particular event relating to the subject, wherein said programming is by a second system that electronically stores at least one particular event relating to the subject.

In particular embodiments, the computer readable medium further comprises instructions for resetting the reporter element after the subject fulfills the event.

In a particular embodiment, the computer readable medium comprises instructions for displaying the retrieved medical biographical information on a computer screen located in an emergency vehicle when the subject needs medical care.

In another particular embodiment, the computer readable medium comprises instructions for transmitting the retrieved medical biographical information to a medical facility that is designated to receive the subject.

In another particular embodiment, the computer readable medium comprises instructions for tracking the subject's location using a tracking circuit located on the device worn by or in the possession of the subject.

As used herein, a "medical sensor" refers to an appliance or apparatus that measures or monitors a dynamic bodily function, process or condition. Examples of medical sensors are those that measure or monitor heart rate, temperature, blood oxygen or other blood gasses, an electrocardiogram, or an electroencephalogram.

As used herein, a "removable" device refers to an object or device that a subject or a person attending the subject can place on, or remove from, the body, clothing or an accessory (such as a wallet or in a purse or bag) of the subject at will. The removable device is adapted to be worn on a daily basis, at all times, or at only particular times chosen by the subject, such as, but not limited to, during sleep, exercise, at home, travel, work, outdoors, or indoors.

A system and method are disclosed to assist a medical professional or responder to identify and provide appropriate medication and care to subjects unable to communicate for themselves in non-emergency or emergency scenarios.

One aspect of the present application relates to a first system for providing identification and information. In a particular embodiment, as illustrated in FIG. 1, the first system 100 collects a subject's medical biographical information 110 from various sources, such as the subject's doctors' offices, medical facilities that the subject has visited in the past, and medical records or notes prepared or assembled by the subject. Examples of the subject's medical biographical information 110 include name, sex, date of birth, height, weight, blood type, allergies, sicknesses/medical conditions, use of prescribed medications, emergency contacts, as well as complete medical records if available.

In a particular embodiment, the system 100 electronically stores the subject's medical biographical information 110 in a database of a computer system 120. In some embodiments, the subject's medical biographical information 110 stored in the database is updated by the subject's doctors or the subject as needed. The first system 100 embeds the stored subject's medical biographical information 110 in a readable code 132 of a device 130 that is worn by or in the possession of the subject 140. In some embodiments, the device 130 is a bracelet, pendant, key chain, fob, belt clip, dog tag, necklace, jewelry, button or other object that is worn by the subject. In particular embodiments, the device 130 is kept in the subject's wallet, purse or pocket. In particular embodiments, the device is water resistant, water proof or comprises a water proof coating or sheath that protects the readable code. In particular embodiments, the device is wear resistant, wear proof or comprises a wear proof coating or sheath that protects the readable code.

In another embodiment, the device 130 is a card or a computer readable device, such as, but not limited to, a flash drive, solid state storage device, compact disc, or digital video disc (DVD). In particular embodiments, the readable code is contained on the removable device in electronic form.

In other particular embodiments, the readable code is present on the removable device in a printed form. In further embodiments, the printed form may be in the form of a bar code, a binary code, a matrix code, pictogram or a quick response (QR) code. \In some embodiments, the readable code is present on the removable device in both an electronic form and in a printed form. In some further embodiments, the data stored in electronic form and in printed form on the removable device is the same. In other further embodiments, the data stored in electronic form and in printed form on the removable device is different.

In some embodiments, the readable code is. In other embodiments, the readable code is non-encrypted code. In still other embodiments, the readable code is a combination of encrypted code and non-encrypted code.

In particular embodiments, a responder 150 uses an appliance 160 to scan the readable code 132 of the device 130 worn by, or in the possession of, the subject 140. In particular embodiments, the appliance 160 obtains the subject's medical biographical information 110, which may include, for example, the subject's name, sex, date of birth, height, weight, blood type, allergies, medical histories and conditions, sicknesses, use of prescribed medications, emergency contacts, as well as the complete medical records if available.

In particular embodiments, the responder 150 is a paramedic, emergency medical technician (EMT), fire fighter, policeman/woman, medical professional, or care worker. The term "medical professional" or "medical practitioner" as used herein, includes any person who cares for the medical needs of a subject such as, but not limited to, a physician, surgeon, dentist, chiropractor, osteopath, nurse, nurse's aide, orderly or volunteer.

In some embodiments, the appliance 160 is a handheld scanner. In other embodiments, the appliance 160 is a cellular telephone or a computer, including, but not limited to a laptop, pad or tablet computer. In particular embodiments, the appliance 160 includes an integrated display that displays the subject's medical biographical information 110 to assist the responder on the scene to provide care to the subject 140. in another embodiment, the obtained medical biographical information 110 is displayed on a computer or other appliance or equipment. In a particular embodiment, the appliance and/or display is located in an emergency vehicle 170.

In another embodiment, the first system 100 transmits the medical biographical information 110 to a medical facility 180 that is designated to receive the subject 140. The designated medical facility 180 uses the medical biographical information 110 and the current medical needs of the subject 140 to develop a plan for medical care. In a particular embodiment, said plan for medical care is developed before the subject arrives at the designated medical facility 180.

In a particular embodiment, the medical facility 180 is a hospital. In another particular embodiment, the medical facility 180 is an emergency room. In another particular embodiment, the medical facility 180 is an outpatient facility, including an outpatient urgent care facility. In another particular embodiment, the medical facility 180 is a clinic. In another particular embodiment, the medical facility 180 is a nursing home. In another particular embodiment, the medical facility 180 is a physician's office. In yet another particular embodiment, the medical facility 180 is a dentist's office.

In particular embodiments, transmittal of the medical biographical information 110 and the current medical needs of the subject 140 to the medical facility 180 allows a medical professional 190 at the medical facility 180 to be prepared for the subject's 140 arrival.

In particular embodiments, a medical professional 190 and/or responder 150 submits updated medical biographical information 110 to the database 120. In another embodiment, the subject submits updated medical biographical information 110 to the database 120. In particular embodiments, the updated medical biographical information 110 is automatically synced with data embedded in the readable code 132 of the device 130.

In a particular embodiment, the device 130 comprises a GPS or other tracking circuit 134. In particular embodiments, the medical professional 190 tracks the location of the subject 140. In a particular embodiment, the distance and the travel time before arrival at the medical facility 180 is determined.

In particular embodiments, the first system 100 is used for emergency circumstances. In other particular embodiments, the first system 100 is used for non-emergency circumstances. In a related embodiment, the non-emergency circumstance is transport of a subject 140 from one medical facility 180 to a different medical facility 180.

Figure 2:
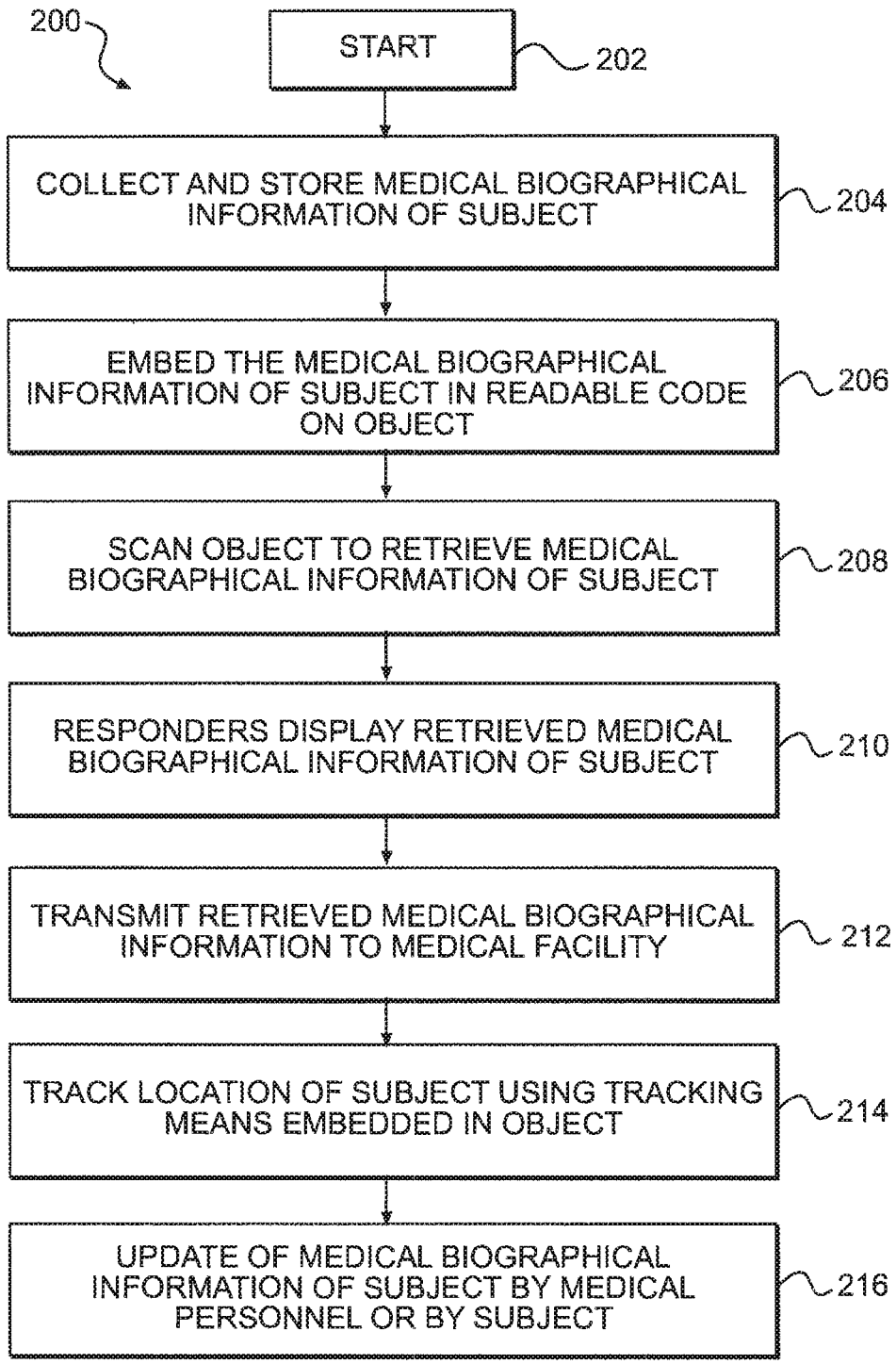
FIG. 2 is a flow charting illustrating an embodiment of the method for providing identification and medical information.

FIG. 2 is a flow chart showing a non-limiting example of an embodiment of a method 200 for providing identification and medical information. In a particular embodiment, method 200 comprises the collection and storage of medical biographical information of the subject 204. In a particular embodiment, the medical biographical information is embedded in a readable code of a device that is adapted to be worn by or in the possession of the subject 206. In particular embodiments, an appliance reads the readable code 208 of the device 206 to retrieve the medical biographical information of the subject 204. In some embodiments, the retrieved medical biographical information 204 is displayed on a computer screen located in an emergency vehicle 210. In particular embodiments, the retrieved medical biographical information 204 is wirelessly transmitted to a medical facility that is designated to receive the subject 212. In some embodiments, the location of the subject is determined using a GPS tracking circuit located on the device worn by the subject 214. In particular embodiments, the medical biographical information 204 is updated by a medical professional or responder 216.

Figure 3:
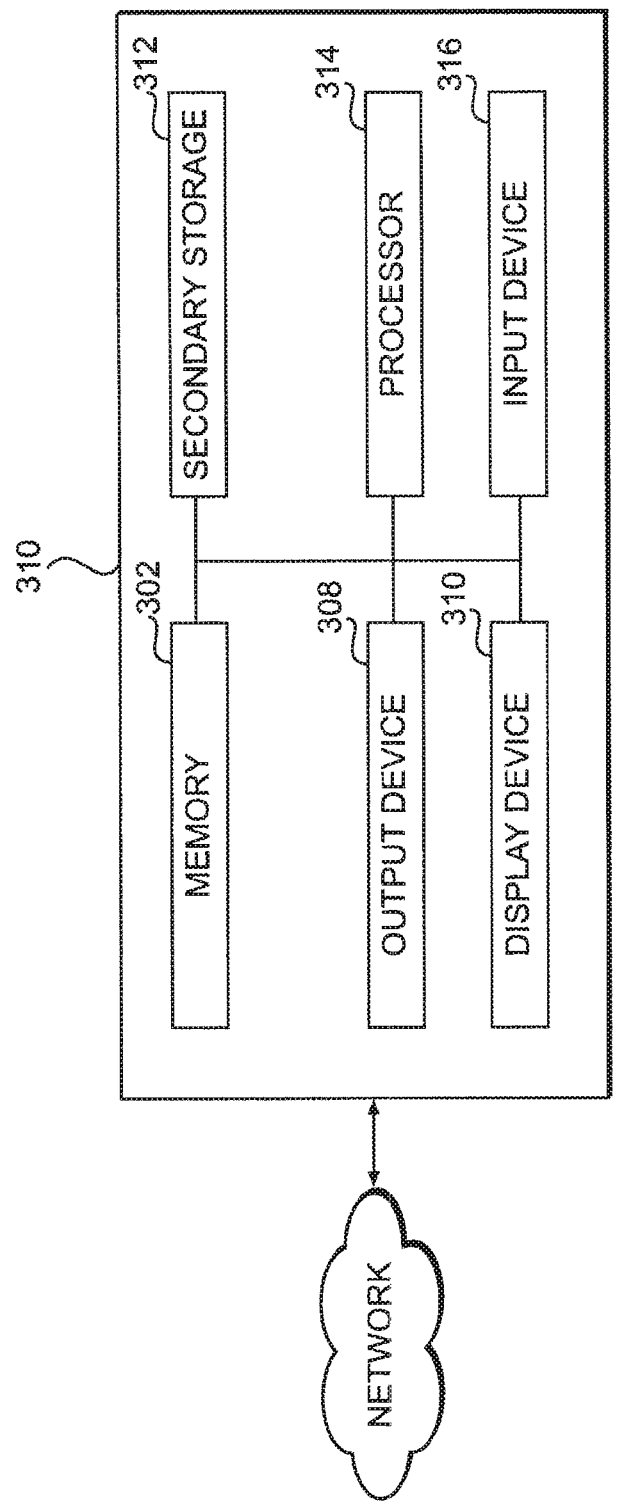
FIG. 3 is a block diagram illustrating exemplary hardware components of the exemplary computer system or server for implementing embodiments of the system and method for providing identification and medical information.

In particular embodiments, as illustrated in FIG. 3, the system disclosed in the present application comprises a computer system or server 300 for implementing embodiments of the system 100 (FIG. 1) and method 200 (FIG. 2) for providing identification and medical information. In an exemplary embodiment, the computer system or server 300 is the computer system 120 of FIG. 1. In particular embodiments, the computer system or server 300 includes and executes software programs to perform functions described herein, including the steps of the method 200 described above. In other embodiments, computer system 300 is a mobile device that performs the steps of the method 200 described above. In particular embodiments. The computer system 300 connects with a network 318, to receive inquires, obtain data, and transmit information as described above. In some embodiments, the network is the internet. In other embodiments, the network is an intranet, WAN, or LAN.

In an exemplary embodiment, the computer system 300 includes a memory 302, a processor 314, and, optionally, a secondary storage device 312. In some embodiments, the computer system 300 includes a plurality of processors 314 and is configured as a plurality of, e.g., bladed servers, or other known server configurations. In particular embodiments, the computer system 300 also includes an input device 316, a display device 310, and an output device 308. In some embodiments, the memory 302 includes RAM or similar types of memory. In particular embodiments, the memory 302 stores one or more applications for execution by the processor 314. In some embodiments, the secondary storage device 312 includes a hard disk drive, floppy disk drive, CD-ROM or DVD drive, or other types of non-volatile data storage. In particular embodiments, the processor 314 executes the application(s) that are stored in the memory 302 or the secondary storage 312, or received from the Internet or other network 318. in some embodiments, processing by the processor 314 may be implemented in software, such as software modules, for execution by computers or other machines. These applications preferably include instructions executable to perform the functions and methods described above and illustrated in the Figures herein. The applications preferably provide GUIs through which users may view and interact with the application(s).

In some embodiments, the processor 314 may execute one or more software applications in order to provide the functions described in this specification, specifically to execute and perform the steps and functions in the methods described above. Such methods and the processing may be implemented in software, such as software modules, for execution by computers or other machines. The GUIs may be formatted, for example, as web pages in HyperText Markup Language (HTML), Extensible Markup Language (XML) or in any other suitable form for presentation on a display device depending upon applications used by users to interact with the system 100.

In particular embodiments, the input device 316 may include any device for entering information into the computer system 300, such as a touch-screen, keyboard, mouse, cursor-control device, microphone, digital camera, video recorder or camcorder. The input device 316 may be used to enter information into GUIs during performance of the methods described above. In some embodiments, the display device 310 may include any type of device for presenting visual information such as, for example, a computer monitor or flat-screen display, mobile device screen, or a printer. The display device 310 may display the GUIs and/or output from a software program. In particular embodiments, the output device 308 may include any type of device for presenting a hard copy of information, such as a printer, and other types of output devices include speakers or any device for providing information in audio form.

Exemplary embodiments of the computer system 300 include dedicated server computers, such as bladed servers, personal computers, laptop computers, notebook computers, palm top computers, network computers, mobile devices, or any processor-controlled device capable of executing a web browser or other type of application for interacting with the system.

In particular embodiments, the first system 100 and/or method 200 may use multiple computer systems or servers as necessary or desired to support the users and may also use back-up or redundant servers to prevent network downtime in the event of a failure of a particular server. In addition, although aspects of an implementation consistent with the above are described as being stored in the memory 302, one skilled in the art will appreciate that these aspects can also be stored on or read from other types of computer program products or computer-readable media, such as secondary storage devices 312, including hard disks, floppy disks, or CD-ROM; DVD or other forms of RAM or ROM. In particular embodiments, the computer-readable media may include instructions for controlling a computer system, such as the computer system 300, to perform a particular method, such as the methods described above.

Figure 4:
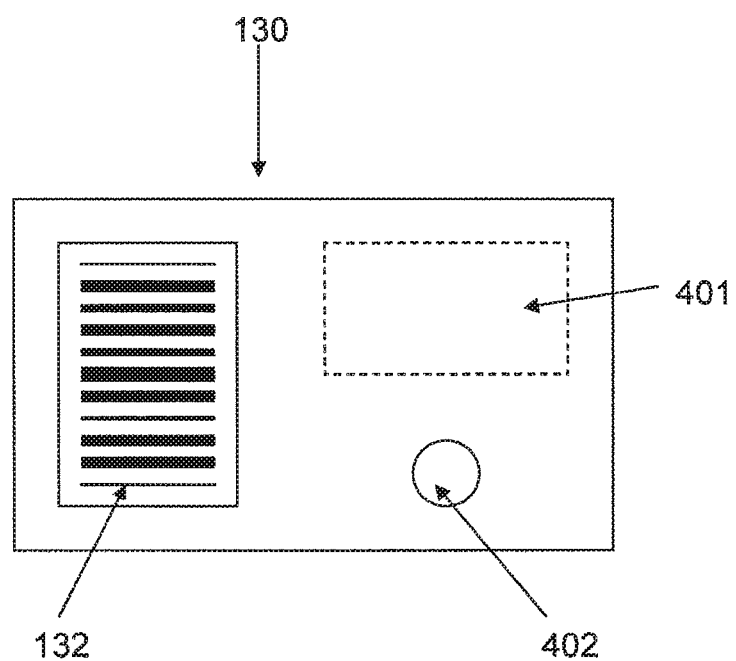
FIG. 4 is a representative schematic view of the elements of the removable device

One aspect of the present application relates to a removable device that is adapted to be worn or in the possession of the subject, as exemplified in the non-limiting example shown in FIG. 4. The device 130 comprises a readable code 132 that contains medical biographical information of the subject, a programmable reporter 401 that electronically stores at least one particular event relating to the subject, and a signal producing element 402 functionally related to the programmable reporter element.

In a particular embodiment, the removable device 130 that is adapted to be worn or in the possession of the subject consists of a readable code 132 that contains medical biographical information of the subject, a programmable reporter element that is programmed by a second system that electronically stores at least one particular event relating to the subject, and a signal producing element functionally related to the programmable reporter element.

In a particular embodiment, the reporter element 401 is programmed to store data regarding at least one particular event relating to the subject and an algorithm for producing an alert signal in the signal producing element 402 to inform the subject of the at least one particular event relating to the subject. In a further embodiment, the alert signal is a light signal. In another embodiment, the signal is an audible signal. In yet another embodiment, the alert signal is a vibrating signal. In yet another embodiment, the alert signal is an alphanumeric display on a LED or LCD display. In yet another embodiment, the alert signal is a signal transmitted from the device to a caregiver or medical practitioner. In yet another embodiment, the device comprises two or more alert signals that are functionally related to the programmable reporter element, comprising two or more of the same type of alert signal or any combination thereof. In a particular embodiment, the reporter element is a separate element of the removable device 130 from the readable code 132.

In particular embodiments, at least one signal producing element of the device is a transmitter. In a related embodiment, the reporter element signals notification of an upcoming event and/or an unfulfilled event related to the subject to a family member, friend, caregiver and/or medical practitioner.

In a particular embodiment, the removable device further comprises a power source for the reporter element and the signal producing element. In a further embodiment, the power source is a battery. In a still further embodiment, the battery is rechargeable. In another still further embodiment, the battery is removable. In another further embodiment, the removable device further comprises a solar cell for recharging the power source.

In a particular embodiment, the removable device that is adapted to be worn or in the possession of the subject consists of a readable code that contains medical biographical information of the subject, a programmable reporter element that is programmed by a second system that electronically stores at least one particular event relating to the subject, a signal producing element functionally related to the programmable reporter element, and a power source.

Another aspect of the present application relates to a system for providing identification and medical information of a subject in a removable device, comprising: a database for collecting and storing medical biographical information of the subject; a removable device that is adapted to be worn by or in the possession of the subject, the device including a readable code that contains medical biographical information; and an appliance for scanning the readable code of the device worn by or in the possession of the subject to retrieve the medical biographical information of the subject, wherein the medical biographical information allows responders to obtain the subject's medical information in order to provide care and wherein the device is not linked to a medical sensor and is worn by the subject in a non-hospital setting, and wherein the device worn by or in the possession of the subject further comprises a reporter element that provides a signal to inform the subject of at least one particular event relating to the subject.

In a particular embodiment, said reporter element is programmed manually.

In another particular embodiment, said reporter element is programmed by a second system that electronically stores at least one particular event relating to the subject. In a further particular embodiment, the second system is the same as the first system. In another further particular embodiment, the second system is separate from the first system.

In a particular embodiment, the at least one particular event is an appointment. In some embodiments, the appointment is a follow-up to a visit by the subject to a medical facility. In a further embodiment, the appointment is a medical appointment. In some embodiments, the medical appointment is selected from the group consisting of a physical examination, a physical therapy session, a mental examination and a mental therapy session. In another particular embodiment, the event is a reminder to schedule an appointment.

In a particular embodiment, the reporter element is programmed to issue a signal a predetermined time prior to the event. In a related embodiment, the predetermined time is about one month prior to the event. In another related embodiment, the predetermined time is about two weeks prior to the event. In another related embodiment, the predetermined time is about one week prior to the event. In other related embodiments, the predetermined time is about 30, 28, 25, 21, 20, 15, 14, 7, 6, 5, 4, 3, 2 or 1 day(s) prior to the event. In another related embodiment, the predetermined time is about 24, 18, 12, 6, 5, 4, 3, 2, or 1 hour(s) prior to the event.

In a particular embodiment, the signal repeats or remains until the subject fulfills the event and the reporter element is reset. In a particular embodiment, the reporter element is reset by the subject. In another particular embodiment, the reporter element is reset by a relative, friend or caregiver. In another particular embodiment, the reporter element is reset by a medical practitioner. In a particular embodiment, the reporter element is reset manually. In another particular embodiment, the reporter element is reset by resetting the second system.

In another particular embodiment, the reporter element is programmed to issue an alert signal a predetermined time after the event if the event was not fulfilled or the reporter element was not reset. In a related embodiment, the warning signal is issued on a repeating basis. In a related embodiment, the predetermined time is 15, 30, 45 or 60 minutes after the scheduled time of the event. In another related embodiment, the predetermined time is 1, 2, 3, 4, 5, 6, 12, 18 or 24 hour(s) after the scheduled time of the event. In another related embodiment, the predetermined time is 1, 2, 3, 4, 5, 6, 7, 14, 15, 20, 21, 25, 28 or 30 day(s) after the scheduled time of the event.

In some embodiments, the reporter element is programmed to issue an alert signal before an event in addition to, if the event is not fulfilled by the subject, after said event. In particular embodiments, the signals before and after the event are the same. In other particular embodiments, the signals before and after the event are different.

In a particular embodiment, if the subject fails to fulfill the event, the second system alerts a medical practitioner.

An alternative embodiment of the present application relates to a personal health record device that is portable. In some embodiments, the personal health record is a collection of healthcare information maintained by the subject, the subject's guardian or a caregiver. In further embodiments, the healthcare information may include at least one of several bits of information including, but not limited to, biographical information, personal contacts, contact information for physicians or caregivers, medications the subject is taking or has taken in the past, any past or present medical conditions, allergies and sensitivities, advanced directives (such as do not resuscitate), blood type, HLA Class I and Class II type, donor information, medical test results, information regarding particular symptoms, and much more. In some embodiments, records include images, such as X-rays or CT scans. In some embodiments, the information contained is editable. In some embodiments, the information includes scanned images, such scanned images of lab test results, doctor's notes and medical records.

In some embodiments, the device includes information regarding scheduled appointments.

In some embodiments, the device is in the possession of the subject. In other embodiments, the device is in the possession of the subject's parent, child, spouse, significant other, guardian or caregiver.

In some embodiments, the device is a card comprising solid state memory comprising software or an application (app) for storage of, or access to, a health record of a subject. In further embodiments, the card is the size of a credit card. In some embodiments, the software or health record is accessible by at least one of Apple iOS, Android, Windows, Apple MacOS or Linux. In some embodiments, the device comprises a USB connector for connecting the solid state memory with another device, such as a computer, tablet or smart phone. In other embodiments, the device comprises a connector for connecting the solid state memory with an SD, Mini SD, Micro SD or CompactFlash receptacle on another device, such as a computer, tablet or smart phone. In some embodiments, connecting the solid state memory with a computer, tablet or smart phone, allows the computer, tablet or smart phone to run the software or app stored on the solid state memory and access a health record of the subject that is stored on the device or in a remote database.

In some embodiments, the device comprises a scannable QR code or barcode that provides access to a health record of the subject that is stored in a remote database.

In some embodiments, the device comprises a displayed alpha and/or numeric code specific to the health record of the subject. In some embodiments, the code is printed, embossed, debossed, engraved, adhered or stamped on the device. In some further embodiments, the device further comprises a displayed telephone number and/or website address, wherein entry of the code at said telephone number (verbal or manual) or website (manual) grants access to a health record of the subject that is stored in a remote database. In some further embodiments, the code is furnished to a service representative with access to the database. In some embodiments, the device provides multiple methods for accessing the health record of the subject. In some embodiments, the device comprises at least two of a solid state memory accessible by another device, RFID, QR code, barcode, and an alpha and/or numeric code. In some embodiments, the device further comprises instructions for accessing the health record by one or more methods.

Another aspect of the present application relates to a portable device for storing medical information from a subject. The portable device comprises (a) a solid-state memory that stores medical information of the subject; (b) a readable code on a surface of the device for identification; and (c) an interface to interact with a computer, smart phone or tablet.

In some embodiments, the readable code is a bar code, a binary code, a matrix code, a pictogram or a quick response (QR) code.

In some embodiments, the portable device further comprises a Radio Frequency Identification (RFID) tag, the RFID tag comprising a chip configured to be scanned and read by an RFID reader, wherein the chip is wirelessly linked to a server comprising medical and biographical information specific to the subject.

EXAMPLES

In cases where an individual is experiencing a medical emergency and becomes incapacitated, requiring immediate and informed medical care, the subject may be provided with a device containing a readable code that may be inserted in an object worn by, or in the possession of the incapacitated individual.

Figure 5:
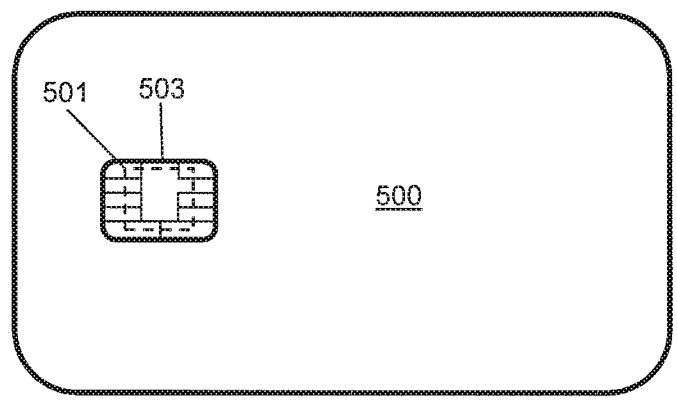
FIG. 5 is a representative schematic view of another embodiment of the removable device.

For example, the device may be contained in a card, such as an insurance card, in the form of a Radio Frequency Identification (RFID) tag containing a chip that can be scanned and read by an RFID (see FIG. 5). As shown in FIG. 5, this inconspicuous chip 501, inserted in the RFID Tag 503 on the card 500, is associated with a specific patient and that patients medical and biographical information. The patient's medical and biographical information may be stored in a server, preferably a secure server.

The server may include any medical or biographical information specific for the subject. Examples of medical records or personal information may include, for example, records of previous lab work, x-rays, CT-scans or MRIs, any known allergies, blood type, height, weight, date of birth, social security number, last known address, known illnesses, diseases, medical procedures or operations performed, medications previously or currently prescribed, listed Primary Care Provider (PCP), contact information from the subject, contact information from the subject's next of kin and combinations thereof.

When provided with the patient's RFID device (e.g., worn object or insurance card) in combination with RFID reader, a medical professional, such as an Emergency Responder or EMT, can scan the RFID device with a suitable RFID reader, such as a CN70 RFID reader wirelessly connected to a server; retrieve the medical or biographical information specific for the patient from the server; display the information on the RFID reader screen; and make instant and real time medical decisions based on this information. Advantageously, this process removes much of the guesswork and risks from the medical equation, promoting more efficient and informed care that can reduce misdiagnoses, and potentially reduce or prevent costly malpractice lawsuits or even death.

Following the treatment provided to this patient, the EMT can select the most appropriate receiving hospital from a group of facilities listed on the device. In this case, selection of the hospital for further evaluation and additional medical care may be based on the distance from the medical event and care needed.

Once an appropriate receiving hospital is selected, the emergency department at the selected receiving facility may be notified of the pending arrival of that specific patient by a message (e.g., email or text message) transmitted from the RFID device to the emergency department. The message can inform the emergency department of the pending arrival of that specific patient and provide to the emergency department the patient's medical and biographical information retrieved from the server, along with information concerning any treatment rendered on the scene by the EMT. While that notification is being sent to the receiving hospital, a simultaneous message may be sent to the patient's next of kin, alerting them of the unexpected medical emergency.

This process can address certain deficiencies relating to Electronic Medical Records (EMR) management, which is largely disconnected and nonintegrated.

Another aspect of the above described device is to utilize the RFID tag when checking in or registering for a medical visit at a hospital or other medical facility. In this case, electronic transmission of the patients medical and biographical information can help reduce paper work, including unnecessary documents by employing the readable code on e.g., the same insurance card format as earlier stated upon arrival at a medical appointment, where the patient's data can be retrieved from the system by the registration clerk with the use of an interface allowing the patient's pertinent medical information to be downloaded into a selected EMR database at use for that specific medical history as well.

In a further aspect, the readable code or RFID tag may be used for filling prescriptions at a pharmacy. Due to the record keeping capacity of the server, and all the data therein, including all medications (past & present) patients have been using, use of the RFID tag can prevent pharmacies from filling prescriptions for medications that might conflict with other medication(s) the patient is already using, including those that could have been filled at another pharmacy that doesn't collaborate with, or have access to, the subject pharmacy database. Accordingly, this system can assist in monitoring the prescriptions prescribed by different providers that aren't collaborating for the care of a particular patient. Arming the pharmacist with the entire patient's prescription profile, so he or she, can prevent any further duplications or conflict associated with co-administration addresses an important unfilled need.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for providing identification and medical information about a subject, comprising:
   providing a user with a portable device wirelessly linked to a server comprising medical and biographical information specific to the subject, wherein the portable device includes an integrated display and is not linked to a medical sensor,
   displaying the medical and biographical information specific to the subject on the integrated display,
   programming a reporter element to electronically store at least one particular event relating to the subject,
   providing a signal to a functionally linked signal producing element by using the programmable reporter element to inform the user of the device of at least one particular event relating to the subject, wherein a first system includes the reporter element and the signal producing element, wherein the at least one particular event is electronically stored by a second system that includes the server, and wherein if the subject fails to fulfill the at least one particular event, the portable device alerts the user via the integrated display, and
   developing a plan of medical care for the subject based on the at least one particular event relating to the subject.

2. The method of claim 1, wherein the medical and biographical information comprises medical records or personal information selected from the group consisting of previous lab work, x-rays, CT-scans, MRIs, allergies, blood type, height, weight, date of birth, social security number, last known address, known illnesses, diseases, medical procedures or operations performed, medications previously or currently prescribed, listed Primary Care Provider (PCP), contact information from the subject, contact information from the subject's next of kin, and combinations thereof.

3. The method of claim 1, further comprising:
   retrieving the subject's medical and biographical information from the server and displaying the subject's medical and biographical information on a screen of a Radio Frequency Identification (RFID) reader; and
   treating the subject based on a consideration of the subject's medical and biographical information.

4. The method of claim 3, further comprising:
   selecting a suitable receiving hospital from a group of facilities listed on the device and notifying an emergency department in the selected receiving hospital of the subject's pending arrival at the receiving hospital.

5. The method of claim 4, further comprising providing the subject's medical and biographical information obtained from the server to the emergency department, along with a description of the treatment provided to the subject.

6. The method of claim 4, further comprising notifying one or more of the subject's next of kin concerning the emergency.

7. The method of claim 1, wherein the subject is automatically registered in a receiving hospital by the server.

8. The method of claim 1, further comprising:
retrieving the subject's medical and biographical information from the server and displaying the subject's medical and biographical information on a screen of a Radio Frequency Identification (RFID) reader; and
prescribing one or more drugs for the subject based on a consideration of the subject's medical and biographical information.

9. The method of claim 1, further comprising:
checking into a hospital or registering for a medical appointment, based on identification of a subject's Radio Frequency Identification (RFID) tag; and
retrieving the subject's medical and biographical information from the server.

10. The method of claim 9, further comprising displaying the subject's medical and biographical information on a screen of a Radio Frequency Identification (RFID) reader.

11. The method of claim 9, further comprising downloading the subject's medical and biographical information into an electronic medical records (EMR) database.

12. The method of claim 9, further comprising electronically entering medical information pertaining to the hospital visit or medical appointment into an EMR database.

13. The method of claim 1, wherein the device comprises an insurance card comprising a Radio Frequency Identification (RFID) tag.

14. A portable device for storing medical information from a subject, comprising:
(a) a solid-state memory that stores medical information of the subject;
(b) a readable code on a surface of the device for identification;
(c) an interface to interact with a computer, smart phone or tablet; and
(d) a chip wirelessly linked to a server comprising medical and biographical information specific to the subject,
wherein the device is not linked to a medical sensor.

15. The portable device of claim 14, wherein the readable code is a bar code, a binary code, a matrix code, a pictogram or a quick response (QR) code.

16. The portable device of claim 15, wherein the bar code is a QR code.

17. The portable device of claim 14, further comprising a Radio Frequency Identification (RFID) tag, the RFID tag comprising a chip configured to be scanned and read by an RFID reader, wherein the chip is wirelessly linked to a server comprising medical and biographical information specific to the subject.

* * * * *